US006815957B2

(12) United States Patent
Hobelsberger et al.

(10) Patent No.: US 6,815,957 B2
(45) Date of Patent: Nov. 9, 2004

(54) METHOD AND DEVICE FOR INSPECTING LAMINATED IRON CORES OF ELECTRICAL MACHINES FOR INTERLAMINATION SHORTS

(75) Inventors: Max Hobelsberger, Wuerenlingen (CH); Ingo Kirchhoff, Zurich (CH); Eric Nodwell, Vancouver (CA); Zlatimir Posedel, Neuenhof (CH)

(73) Assignee: Alstom (Switzerland) LTD, Baden (CH)

( * ) Notice: Subject to any disclaimer, the term of this patent is extended or adjusted under 35 U.S.C. 154(b) by 21 days.

(21) Appl. No.: 10/147,085

(22) Filed: May 17, 2002

(65) Prior Publication Data

US 2003/0057961 A1 Mar. 27, 2003

Related U.S. Application Data

(60) Provisional application No. 60/324,061, filed on Sep. 24, 2001.

(30) Foreign Application Priority Data

Apr. 5, 2002 (CH) ............................................. 0586/02

(51) Int. Cl.[7] .......................... G01R 31/06; G01N 33/12
(52) U.S. Cl. ....................... 324/545; 324/233; 324/242; 324/521
(58) Field of Search .................................. 324/545, 233, 324/242, 521

(56) References Cited

U.S. PATENT DOCUMENTS

| 4,628,261 A | | 12/1986 | Hüschelrath et al. |
| 4,897,607 A | * | 1/1990 | Grunewald et al. .......... 324/545 |
| 4,996,486 A | | 2/1991 | Posedel |
| 5,321,362 A | | 6/1994 | Fischer et al. |
| 5,895,439 A | | 4/1999 | Fisher et al. |

FOREIGN PATENT DOCUMENTS

| CH | 676526 A5 | 1/1991 |
| DE | 35 42 159 A1 | 6/1987 |
| GB | 1 521 203 | 8/1978 |
| GB | 2 044 936 A | 10/1980 |

OTHER PUBLICATIONS

CH Search Report dated Oct. 4, 2002.

* cited by examiner

*Primary Examiner*—N. Le
*Assistant Examiner*—Timothy J. Dole (57) ABSTRACT

The present invention relates to a method, an apparatus and a computer program for inspecting laminated iron cores (1) of electrical machines for interlamination shorts, in which the laminated iron core (1) is magnetized by means of an auxiliary winding, and the iron surface is scanned by means of at least one measurement coil arrangement (2) with a downstream measurement device. In this case, unique and quantifiable localization of interlamination shorts is achieved by using both the phase (8) and the amplitude (7) of the electrical signal which is induced in the at least one measurement coil arrangement (2), in combined form.

22 Claims, 6 Drawing Sheets

METHOD AND DEVICE FOR INSPECTING LAMINATED IRON CORES OF ELECTRICAL MACHINES FOR INTERLAMINATION SHORTS

This application claims priority under 35 U.S.C §§119 and/or 365 to application Ser. No. 2002 0586/02 filed in Switzerland on Apr. 5, 2002; the entire content of which is hereby incorporated by reference.

This application claims priority under 35 U.S.C. §119 to U.S. Provisional Application No. 60/324,061 entitled Low Flux Signal Analysis for Fault Assessment of Laminated Iron Core Stacks and filed on Sep. 24, 2001, the entire content of which is hereby incorporated by reference.

FIELD OF THE INVENTION

The invention relates to a method for inspecting laminated iron cores of electrical machines for interlamination shorts, in which the laminated iron core is magnetized by means of an auxiliary winding and the iron surface is scanned by means of a measurement coil arrangement with a downstream measurement device.

The invention also relates to an apparatus for carrying out the method, and to a computer program for data evaluation.

BACKGROUND OF THE INVENTION

Laminated iron cores, in particular of electrical machines, are frequently inspected for interlamination shorts during production and in the course of maintenance work during operation, using the measurement method of stator laminate ring excitation with rated induction. This method which indicates the effect of interlamination short currents in the form of local temperature differences, demands a powerful voltage source which can be regulated, and field windings with large cross sections (so-called hot spot method using, for example, infrared cameras). In the case of stators with built-in winding bars, this inspection can identify only those fault points (short circuit between a number of laminates) on the tooth surface, and not the laminate faults in the slot base or on the slot sides. This method identifies only interlamination shorts with a specific contact resistance and resultant local temperature differences, and hence not all interlamination short points. The temperature increase on its own is not sufficient for quantitative assessment of the interlamination short point. However, quantitative assessment of these fault points is worthwhile since, in the end, the volt-amperes in a fault point are a critical criterion for determining whether such a region is able to initiate so-called "core melting", that is to say melting occurring during operation as a result of excessive heating at the fault point.

U.S. Pat. No. 5,321,362 describes a so-called low-induction method for determining the short-circuit currents at interlaminate contacts, in which the laminated core is first of all weakly magnetized using a coil placed around the laminated stator core, and the stray field on the laminated core is then measured using a measurement coil arrangement. This method has the advantage that it does not require such high induction currents and, furthermore, it is possible to localize not only fault points that are located on the tooth surface. In this case, it is also possible to identify fault points which are not heated at that time during the method mentioned above, and the measurement process can be carried out with the rotor installed. U.S. Pat. No. 5,321,362 is in this case based exclusively on a current measurement, and therefore does not make it possible to draw any reliable conclusion with regard to the volt-amperes flowing in the fault point.

Secondly, CH 676526 A5 describes a method in which fault points can be localized not only on the tooth surface but also in the slot base and on the slot sides, and in a quantitative manner, as well. This is once again a low-induction method, but in this case it is not simply the current that is measured, but a reference measurement is also proposed, which allows the volt-amperes flowing in a fault point to be determined directly and quantitatively, by appropriate back-calculation.

One fundamental problem in the context of such low-induction methods is the fact that they frequently do not allow unique localization of fault points, since differences in the behavior of the magnetic iron core (for example resulting from cooling slots) can also lead to signals which, with these methods, may possibly also be interpreted as fault points.

SUMMARY OF THE INVENTION

One object of the present invention is therefore to propose a method for inspecting laminated iron cores of electrical machines for interlamination shorts, in which method the laminated iron core is magnetized by means of an auxiliary winding and the iron surface is scanned by means of at least one measurement coil arrangement with a downstream measurement device, and which allows fault points, that is to say any interlamination shorts which may be present, to be localized as uniquely as possible.

The object is achieved in that both the phase and the amplitude of the electrical signal which is induced in the at least one measurement coil arrangement are used in combined form to localize interlamination shorts. Thus, in contrast to the methods according to the prior art, not only the amplitude or not only the phase is used to localize the interlamination shorts, but the phase and amplitude information is used in a combined manner to identify them.

This is because, surprisingly, it has been found that the amplitude and phase when combined, that is to say effectively considering the vector of the current induced in the measurement coil arrangement, allow unique localization of the interlamination shorts, and in a quantitative manner as well.

According to a first preferred embodiment of the present invention, an interlamination short is identified in that a real part of the induced electrical signal occurs which is high in comparison to the intact regions. Specifically, it has been found that such a high real part actually uniquely characterizes those fault points, that is to say regions, at which individual laminates are connected to one another via a short circuit. In this case, this high real part can preferably be determined in particular by means of a polar representation.

The direction which in this context is referred to as the "real part" is, so to speak, a "pronounced direction" and is defined, for example, by the embodiment described further below, in which a reference is fed in using a calibration current coil (loop) with an appropriate width and with an appropriate laminate current.

According to a further preferred embodiment of the invention, the method can be combined with a gradient measurement, that is to say with a measurement which also allows unique and quantifiable localization of the fault point in the radial direction with respect to the stator. This is done by arranging at least one further measurement coil arrangement radially at a distance, which further measurement coil arrangement is electrically isolated from a first measurement coil arrangement but is mechanically connected to the fist measurement coil arrangement, and by using both the phase and the amplitude of the at least two electrical signals, which are induced in the at least two measurement coil arrangements, to localize interlamination shorts, in particular to localize them in the radial direction.

Another preferred embodiment is characterized in that the induced electrical signals are compared with signals which correspond to the interlamination short currents, with a loop with an appropriate width being mounted on the surface of the laminated iron core as a reference for this purpose, and being fed with an appropriate interlamination short current. This method allows quantification of the fault points, that is to say, in particular, it allows determination of the volt-amperes which effectively flow in a fault point. It is thus possible to detect the actual fault points with reference to any possible "core melting".

The auxiliary winding for magnetization of the laminated iron cores can, according to a further preferred embodiment, be provided such that the laminated iron core is magnetized in particular via the rotor shaft from a high-power supply source which is connected between the two machine sides, in particular on the insulated shaft. In this case the laminated iron core is preferably magnetized in the range from 0.03 to 0.7 Tesla, in particular approximately 0.1 Tesla, with a voltage of 220/110 volts at 50/60 Hz.

In a further preferred embodiment of the present invention, the at least one measurement coil arrangement, or in the case of a gradient measurement the at least two measurement coil arrangements, is or are shifted on the laminated iron core in the axial direction. In this case, the induced signals are determined, in particular in the form of a fingerprint, as a function of the position of the measurement coil arrangement, with regions with critical interlamination shorts being determined, in particular, via the real part and being distinguished from regions with noncritical interlamination shorts, and with the critical regions being marked for immediate rectification, and the regions which are (still) noncritical (at that time) being documented for later analysis.

Furthermore, the present invention relates to an apparatus for carrying out a method as described above, comprising first means for determining the position of the measurement coil arrangement on the laminated iron core, comprising second means for detecting the amplitude and the phase, in particular by means of a phase detector, of the electrical voltage which is induced in the measurement coil arrangement, and also comprising a data processing unit, which analyzes the measured data and, in particular, is able to localize critical interlamination shorts and to determine the volt-amperes flowing in them, by comparison with a reference. Normally, the position of the measurement coil arrangement can in this case be detected using the first means, and the measured value can be detected using the second means. This information is supplied to the data processing system, thus making it possible to obtain an overall image of the state of the stator. The first means may in this case be designed, for example, in the form of a measurement unit relating to the movement position of a robot carriage to which the measurement coil arrangement or arrangements is or are fitted.

Further preferred embodiments of the method according to the invention and of the apparatus according to the invention are described in the dependent patent claims.

In addition, the present invention relates to a computer program for carrying out the analysis in a data processing unit, as is used in the apparatus mentioned above. The computer program is characterized in that the data, that is to say the phase and amplitude of the electrical voltage which is induced in the measurement coil arrangement, is changed to a vector representation for example in the form of a polar diagram, preferably after having been adjusted using a reference, and fault points are automatically distinguished from noncritical regions, in that only high amplitude values which at the same time have a high real part are identified as being critical.

This is done, for example, by determining fault points on the basis of the real part of the signal exceeding a predetermined limit value, with the limit value preferably being the mean value of all the data over the entire length of the laminated iron core. This determination process may in this case be carried out either automatically, or else, so to speak, manually by the user, that is to say the user assesses the polar diagram to decide which regions should be included in the fault table, and which should not.

Further preferred embodiments of the computer program according to the invention are described in the dependent patent claims.

BRIEF DESCRIPTION OF THE DRAWINGS

The invention will be explained in the following text using exemplary embodiments in conjunction with the figures, in which:

FIG. 2
a) shows the amplitude measured by the measurement coil arrangement as a function of the position along the stator axis;
b) shows the phase measured by the measurement coil arrangement as a function of the position along the stator axis;

DETAILED DESCRIPTION OF THE INVENTION

The proposed method for determining fault points in laminated iron cores based on the detection of the magnetic stray field which is produced by the current flowing in short-circuited contacts offers a well-considered alternative to methods using high induction (so-called hot spot methods). The method is carried out with a low level of stator magnetization, typically with a magnetization level of 0.1 Tesla. Low magnetization levels such as these make it possible to use a standard 220/110 volt appliance for magnetization of the stator using the auxiliary winding (for general items relating to the method, see CH 676526). The measurement of the stray field makes it possible to determine the state of the laminated iron core of the stator in detail and very accurately. Fundamentally, this relates to the following points:

identification of problematic regions separation of noncritical signals ("apparent signals")

quantification of the identified fault points and their classification as dangerous or not dangerous localization of all identified fault points, including those on the slot base and on the side wall of the slot These aims are achieved by producing a detailed map of the stray field above the stator teeth. The stray field is in this case measured using a measurement coil arrangement which is mounted on a robot mount and which is passed along the gap between the rotor and stator. Both the amplitude and the phase of the voltage induced in the measurement coil arrangement are recorded during this process.

Figure 1:
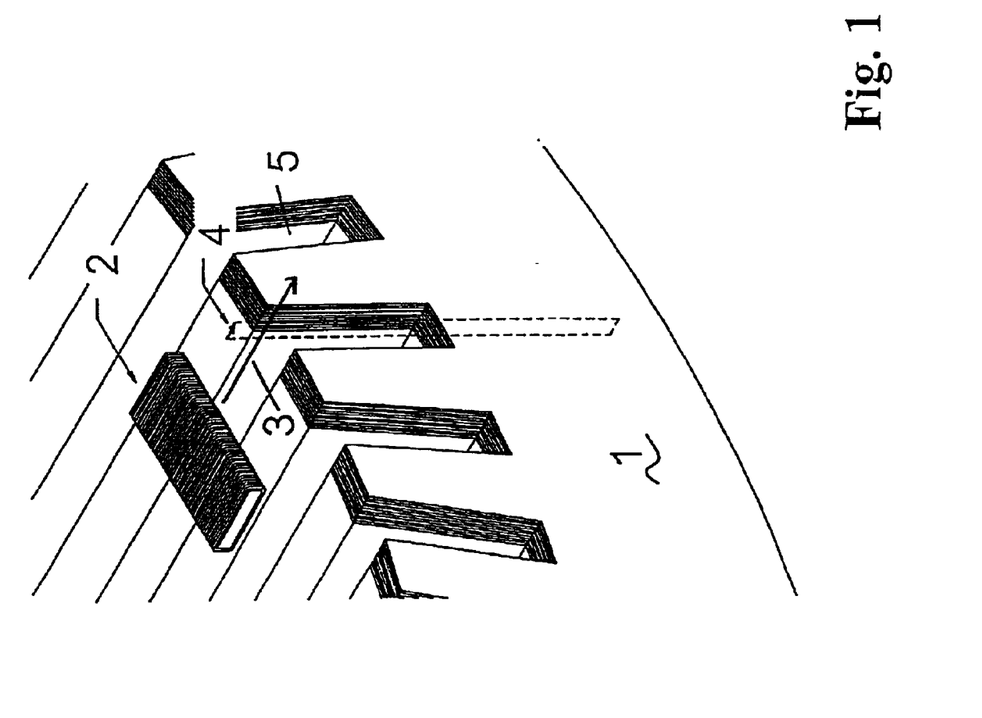
FIG. 1 shows a perspective view of a stator with laminated iron cores, in which the windings from the stator slots are not shown, to improve the illustration, and in which a fault current is indicated.

FIG. 1 shows the procedure in this case. By means of an auxiliary winding (not shown, but in this context see FIG. 1 in CH 676526), the stator, that is to say the laminated iron core 1, is initially slightly magnetized as an entity. A voltage of either 220 or 110 volts at 50 to 60 Hz is normally used for this purpose. After this, the measurement coil arrangement 2 is shifted in the axial movement direction 3 over the laminated core 1 of the stator, while the induced voltage and the induced phase are recorded at the same time. If a fault current 4 occurs between the individual layers of the laminated iron core 1, that is to say a short-circuit current occurs, then this induces a voltage with a specific phase in the measurement coil arrangement 2. This can be done with the conductors (not shown in FIG. 1) fitted in the stator slots 5. Even at the slot base and on the side walls of the stator slots 5, the accuracy of the localization of short-circuit points can in this case be increased by arranging two measurement coil arrangements 2 one above the other, and in this way measuring the gradient of the stray field on the stator teeth in detail. The closer a fault point is located to the measurement coil arrangements 2, the more pronounced is the gradient, thus allowing the fault point to be localized in the radial direction (in this context, see the method as is described in CH 676526).

Figure 2:
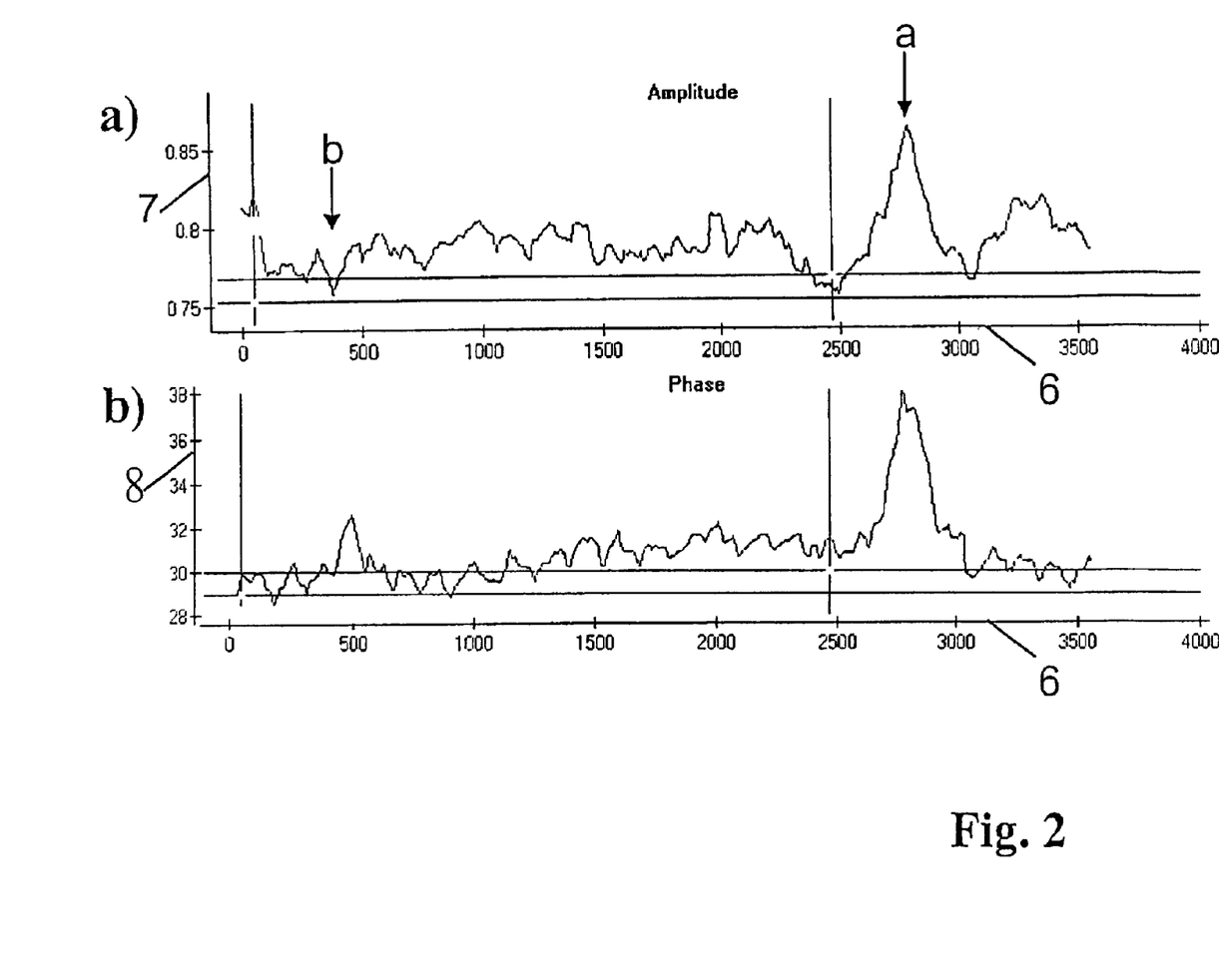

A data processing unit (not shown) records both the amplitude 7 and the phase 8 as a function of the position 6 of the measurement coil arrangement 2 for each stator slot 5. In this case, the phase 8 is normally determined using an upstream phase detector. The measured phase angle is independent of the yoke induction during the measurement. FIG. 2 shows such a graph of the amplitude 7 or phase 8 as a function of the axial position 6 of the measurement coil arrangement 2 in millimeters in the stator. The illustrated data were determined on a 50 MW machine. When looking at the two curves a) and b), it is obvious that it is very difficult to distinguish between actual fault points a and suspected fault points (noncritical regions) b.

Such suspected fault points b result from circumferential asymmetries in the construction of the stator, for example those which occur in the case of cooling slots, or from local mechanical loads on the laminated iron core 1. It is tremendously important to distinguish per se between noncritical regions and the actual fault points a, in order to avoid unnecessary repairs and the costs associated with them. The present method is now in fact actually able to identify noncritical regions, and to distinguish them from actual fault points, such as the fault point a in FIG. 2.

The coil of the measurement coil arrangement 2 is designed such that the signal from a fault point is linearly related over a wide range to the axial length over which the current flows in the fault point. Since the voltage per unit length in the stator is constant, the signal can be interpreted as a function of the volt-amperes flowing in the fault point:

$$\text{Signal} \propto I \times l$$

$$\propto (I \times l) \times \left(\frac{V}{l}\right) \text{ since } \frac{V}{l} = \text{const}$$

$$\propto \text{volt-amperes}$$

These volt-amperes are the total volt-amperes associated with the current (short-circuit current) in the fault point. The volt-amperes in the contact point cannot exceed this value. The identified fault point can therefore be quantified with respect to the maximum possible power dissipated in the fault point at the short circuit. This power is converted to the rated induction, and a value of 15 W is normally used as the limit value in this case. This is the first time that it has been possible to define a really direct relationship between the measured value and the possible damage from such a fault point during operation of the system.

Figure 3:
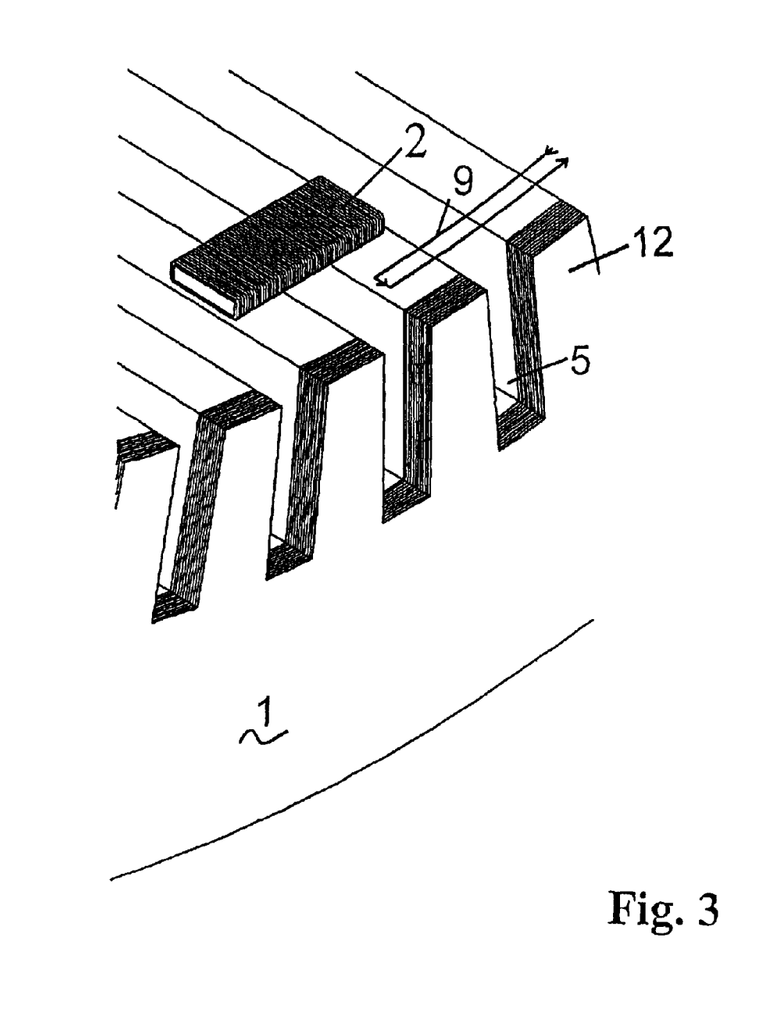
FIG. 3 shows a perspective view of a stator with laminated iron cores as shown in FIG. 1, with a calibration current coil.

The completely quantitative interpretation of the raw data as a function of the maximum contact volt-amperes requires comparison with a reference measurement. For this purpose, as is shown in FIG. 3 and as is described, for example, in U.S. Pat. No. 4,996,486 (whose contents are intended to be included explicitly in the present application, with regard to calibration), a calibration current coil 9 is placed over the stator teeth 12, and is driven with a known current. The current passed through the calibration current coil 9 in this case corresponds to a value equivalent to the interlamination short current. The interlamination short currents of short-circuited laminates are defined from the known voltage values between the laminates and the impedance of the short-circuited laminates. The signal from the measurement coils is then recorded with and without this current, and is compared with that of the interlamination short current. In other words, a fault point is simulated, which can then be taken into account in the analysis.

As has already been mentioned above, the major object is to identify actual fault points. This is done by recording the induced voltage and its phase and by then calculating the real part and imaginary part, that is to say the real part 10 and the imaginary part 11.

In the process, it has been found that signals from fault points are characterized in that the real part 10, that is to say the real component or the real power, is considerably greater than the inductive imaginary part 11, that is to say the imaginary component or the wattless component. In other words, it has been found that the vector in the fault-free regions fluctuates essentially only with respect to the imaginary part, while fault points show major changes to the real part 10. This can be processed and visualized in an impressive manner which can also be used well for data processing programs using vector representation, for example using polar diagrams, with criteria.

Figure 4:
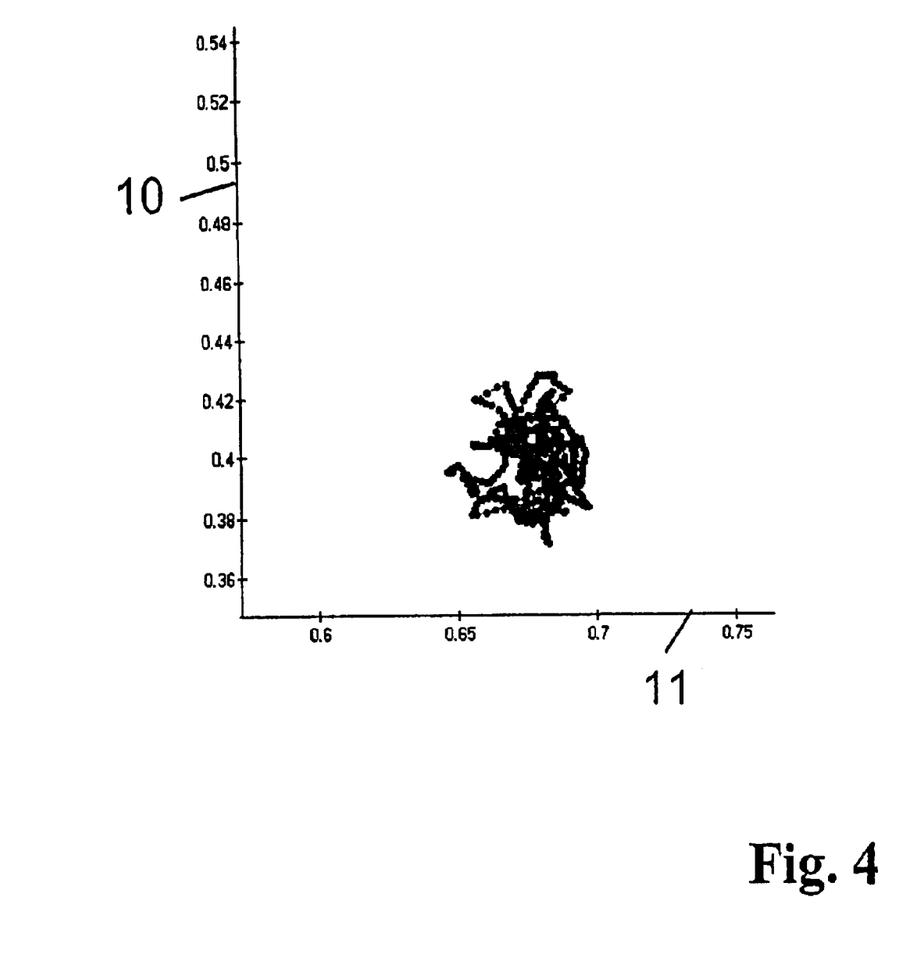
FIG. 4 shows a polar diagram (real part along the y axis, imaginary part along the x axis) of the measurement data shown in FIG. 2 for the region between 0 and 2500 mm (position of the measurement coil arrangement in the stator)

In a corresponding way, FIG. 4 shows the data as shown in FIG. 2 in the form of a polar diagram for the range from 0 to 2500 millimeters. The suspected fault point b, which can be seen in particular on the phase plane, is located in this region. However, the polar diagram clearly indicates that this cannot be a fault point, because the vector has scarcely moved at all in the vertical direction, that is to say in the direction of the axis of the real part 10.

Figure 5:
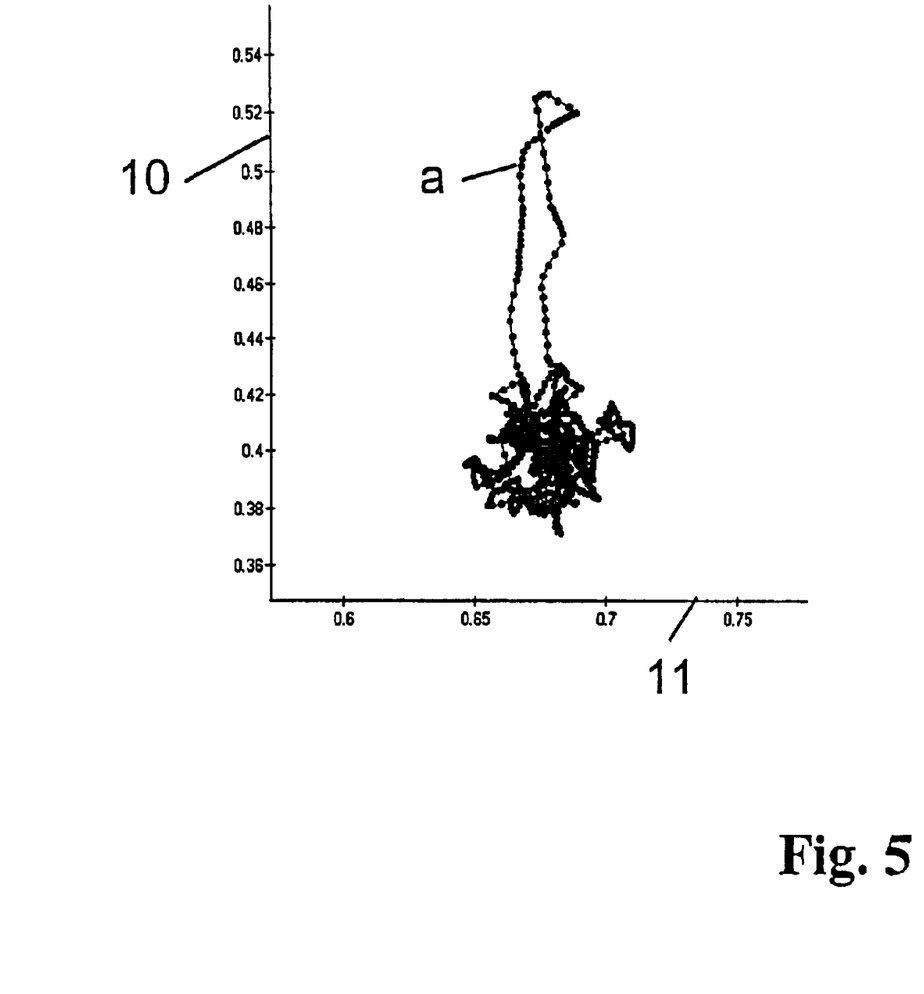
FIG. 5 shows a polar diagram corresponding to FIG. 4 for the region between 0 and 3000 mm (position of the measurement coil arrangement in the stator)

FIG. 5 likewise shows the data as shown in FIG. 2 in the form of a polar diagram for the range from 0 to 3000 millimeters, that is to say over the entire region illustrated in FIG. 2. Here, it can now clearly be seen that the fault point a is associated with a major deflection in the positive vertical direction, that is to say the real part 10 indicates a major deflection for this region. Normally, fault points such as these can be identified by the real part 10 of the signal having a considerable peak in the polar diagram. The sequence of measurement points at the fault point is characterized by a clear vectorial deflection in a pronouncedly different direction than the sequence of measurement points at a fault-free point.

The procedure for data processing in order to identify fault points comprises first of all determining, so to speak, a characteristic typical "background value", that is to say a typical fluctuation range (which is governed by the "sound" regions), of the vectors with respect to the real part and imaginary part, and then defining a threshold value with respect to the real part, and finally marking as critical all those regions in which the vector exceeds this threshold value.

Fundamentally, the threshold value is obtained from the reference measurement described further above. Repair work is carried out only if the vector corresponds to a maximum possible power of 15 watts.

Figure 6:
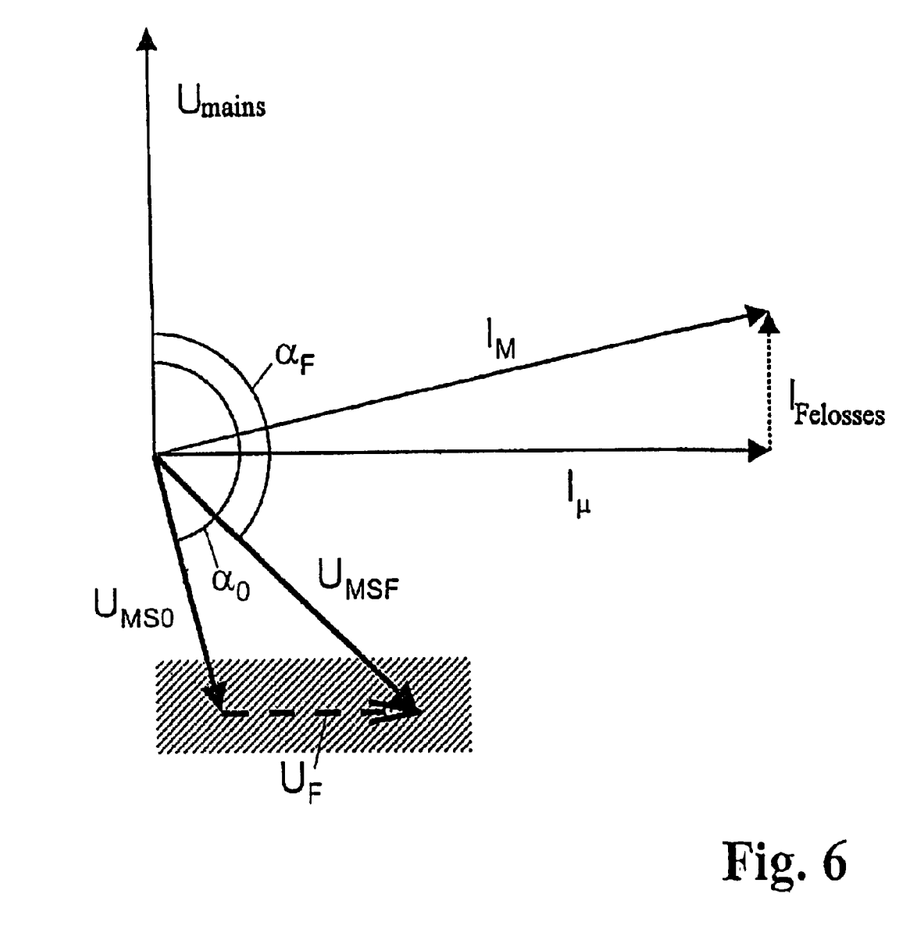
FIG. 6 shows a schematic illustration of those vectors that are relevant for the measurement, on a polar diagram.

FIG. 6 shows, in detail, those vectors which are relevant to the present measurement, in the form of a polar diagram. The magnetization current of the iron $I_\mu$ is modified by a loss component $I_{Felosses}$, so that an actually required magnetization current $I_M$ must be applied. The applied mains voltage $U_{mains}$ is shown on the vertical axis. The phase shift is determined with respect to this voltage. The vectors $U_{MS0}$ and $U_{MSF}$ now designate the voltages induced in the measurement coil. In this case, $U_{MS0}$ represents the voltage which is induced when no faults are present, and $U_{MSF}$ represents the voltage which is induced when a fault is present. The variable $U_F$ which is shown in the vector diagram now represents that part which is in each case referred to in the text as the real part, or the part with the "pronounced direction". The shaded region corresponds to the polar diagram region which is used for determining fault points for the purposes of this invention. Only the vector peaks for the vectors $U_{MS0}$ and $U_{MSF}$ are thus shown in the polar diagram. The angle $\alpha_0$, which is likewise indicated in the figure, represents the phase angle without any faults, and $\alpha_F$ represents the corresponding phase angle when a fault point is present.

In other words, it has been found that the combined analysis of the amplitude and phase information from the recorded signal, possibly after calibration using a calibration current coil, for the first time allows reliable identification of the fault points, and allows them to be detected quantitatively. The proposed method allows comprehensive assessment of the laminated iron core, and therefore means that there is normally no need to carry out any further investigation using a high-induction method.

A further major advantage of the method according to the invention is that the measurement can be repeated as required, and the phase values are essentially independent of the magnetization of the stator. In other words, each measurement may be regarded as the measurement of a fingerprint for the stator. In a corresponding way, it is possible to measure this fingerprint repeatedly, that is to say over several years, and to use it as a trend analysis. Periodic measurement of the stator can thus be used to identify trends in the state of the stator, and to carry out repairs only when they are actually necessary.

LIST OF REFERENCE SYMBOLS

1 Laminated iron core
2 Measurement coil arrangement
3 Movement direction of 2
4 Fault current (short-circuit current)
5 Stator slot
6 Position of 2
7 Amplitude
8 Phase
9 Calibration current coil
10 Real part of the vector diagram
11 Imaginary part of the vector diagram
12 Stator tooth
a Fault point
b Suspected fault point
$I_\mu$ Magnetization current of the iron
$F_{Felosses}$ Losses in the iron on magnetization for the measurement
$I_M$ Actually required magnetization current
$U_{mains}$ Mains voltage
$U_{MS0}$ Voltage induced in the measurement coil without any faults
$U_{MSF}$ Voltage induced in the measurement coil with a fault
$U_F$ Real part, pronounced direction
$\alpha_0$ Phase angle without any faults
$\alpha_F$ Phase angle with a fault

What is claimed is:

1. A method for inspecting laminated iron cores of electrical machines for interlamination shorts, in which the laminated iron core is magnetized by means of an auxiliary winding using alternating current, and the iron surface is scanned by means of at least one measurement coil arrangement with a downstream measurement device, wherein as measurement points both the phase and the amplitude of the electrical signal which is induced in the at least one measurement coil arrangement as a function of the position along the stator axis are used in combined form to localize interlamination shorts, wherein interlamination shorts are localized by means of a real part of the induced electrical signal, which is high in comparison to the intact regions, and wherein the high real part is determined by means of a polar representation of the sequence of measurement points, with the real part defining the vector direction and being determined by a calibration measurement.

2. The method as claimed in claim 1, wherein at least one further measurement coil arrangement, which is electrically isolated from a first measurement coil arrangement is used, and is radially at a distance but is mechanically connected to the first measurement coil arrangement, and both the phase and the amplitude of the at least two electrical signals, which are induced in the at least two measurement coil arrangements, are used to localize interlamination shorts, in particular to localize them in the radial direction.

3. The method as claimed in claim 1, wherein the induced electrical signals are compared with signals which correspond to the interlamination short currents, with a calibration current coil with an appropriate width being mounted on the surface of the laminated iron core as a reference for this purpose, and being fed with an appropriate interlamination short current.

4. The method as claimed in claim 3, wherein the volt-amperes in an interlamination short are determined quantitatively by comparison with the reference.

5. The method as claimed in claim 1, wherein the laminated iron core is magnetized in particular via the rotor shaft from a high-power supply source which is connected between the two machine sides, in particular on the insulated shaft.

6. The method of claim 5, wherein the laminated iron core is magnetized in a range from 0.03 to 0.7 Tesla, with a voltage of 220 volts or 110 volts at a frequency ranging from 50 Hz to 60 Hz.

7. The method of claim 5, wherein the laminated iron core is magnetized at approximately 0.1 Tesla, with a voltage of 220 volts or 110 volts at a frequency ranging from 50 Hz to 60 Hz.

8. The method as claimed in claim 1, wherein the at least one measurement coil arrangement is shifted on the laminated iron core in the axial direction, and, in the process, the induced signals are determined, in particular in the form of a fingerprint, as a function of the position of the measurement coil arrangement, with regions with critical interlamination shorts being determined, in particular, via the real part and being distinguished from regions with noncritical interlamination shorts, and with the critical regions being marked for immediate rectification, and the regions which are still noncritical at the time being documented for later analysis.

9. The method of claim 1, wherein interlamination shorts are identified by a pronouncedly different and clear vectorial deflection of several sequential measurement points from the sequence of measurement points at a fault-free point.

10. The method of claim 9, wherein the clear vectorial deflection of several sequential measurement points at a lamination short differs in phase angle from the fault-free points.

11. The method of claim 10, wherein the length of the vectorial deflection is proportional to the power dissipated in the fault point.

12. The method of claim 10, wherein the length of the vectorial deflection is proportional to the interlamination short current.

13. The method of claim 9, wherein the vectorial deflection substantially corresponds to a direction recorded with a calibration current coil driven with a known current with known phase position.

14. The method of claim 13, wherein the length of the vectorial deflection is proportional to the power dissipated in the fault point.

15. The method of claim 13, wherein the length of the vectorial deflection is proportional to the interlamination short current.

16. The method of claim 9, wherein the length of the vectorial deflection is proportional to the power dissipated in the fault point.

17. The method of claim 9, wherein the length of the vectorial deflection is proportional to the interlamination short current.

18. An apparatus for inspecting a laminated iron core of an electrical machine for interlamination shorts, comprising:

first means for determining a position of a measurement coil arrangement on the laminated iron core along a stator axis of the iron core;

second means for detecting an amplitude and a phase of an electrical voltage which is induced in the measurement coil arrangement; and a data processing unit, which analyzes the determined position, the detected amplitude, and the detected phase via a polar representation of a sequence of determined position values, detected amplitude values and detected phase values to localize critical interlamination shorts and to determine the volt-amperes flowing in them, by comparison with a reference.

19. The apparatus of claim 18, wherein the second means for detecting detects the amplitude and the phase of the electrical voltage via a phase detector.

20. A computer program for causing an apparatus for inspecting a laminated iron core of an electrical machine for interlamination shorts, to perform:

determining a position of a measurement coil arrangement on the laminated iron core;

detecting an amplitude and a phase of an electrical voltage which is induced in the measurement coil arrangement; and analyzing the determined position; the detected amplitude, and the detected phase to localize critical interlamination shorts and determine the volt-amperes flowing in them by comparison with a reference, wherein the detected phase and detected amplitude are changed to a vector representation in the form of a polar diagram.

21. The computer program as claimed in claim 20, wherein fault points are determined by the real part of the signal exceeding a predetermined limit value.

22. The computer program of claim 20, wherein the detected phase and detected amplitude are changed to a vector representation in the form of a polar diagram after having been adjusted using a reference, and wherein fault points are identified automatically.

* * * * *

UNITED STATES PATENT AND TRADEMARK OFFICE
CERTIFICATE OF CORRECTION

PATENT NO.         : 6,815,957 B2                                           Page 1 of 1
APPLICATION NO.    : 10/147085
DATED              : November 9, 2004
INVENTOR(S)        : Max Hobelsberger et al.

It is certified that error appears in the above-identified patent and that said Letters Patent is hereby corrected as shown below:

Title Page,

Item 73 (Assignee): change "Alstom (Switzerland) LTD" to --Alstom Technology Ltd--

Signed and Sealed this
Twenty-first Day of October, 2014

Michelle K. Lee
*Deputy Director of the United States Patent and Trademark Office*